United States Patent
de la Rosa et al.

(10) Patent No.: US 9,039,618 B2
(45) Date of Patent: May 26, 2015

(54) MEDICAL IMAGING DEVICE AND METHOD

(75) Inventors: Jose Angel de la Rosa, Isabela, PR (US); Edgardo R. Lebron, Anasco, PR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 2997 days.

(21) Appl. No.: 10/626,157

(22) Filed: Jul. 24, 2003

(65) Prior Publication Data

US 2005/0033140 A1 Feb. 10, 2005

(51) Int. Cl.
*A61B 5/055* (2006.01)
*A61B 8/00* (2006.01)
*A61B 5/107* (2006.01)
*A61B 5/00* (2006.01)

(52) U.S. Cl.
CPC ............. *A61B 5/1077* (2013.01); *A61B 5/4504* (2013.01)

(58) Field of Classification Search
CPC .................................. A61B 8/00; A61B 5/055
USPC .......... 600/407, 410, 424, 425, 437, 459, 439
See application file for complete search history.

(56) References Cited

U.S. PATENT DOCUMENTS

| | | | | |
|---|---|---|---|---|
| 4,222,274 | A | * | 9/1980 | Johnson ........................... 73/607 |
| 4,233,988 | A | * | 11/1980 | Dick et al. ..................... 600/445 |
| 5,170,439 | A | * | 12/1992 | Zeng et al. ..................... 382/131 |
| 5,462,056 | A | * | 10/1995 | Hawman et al. ............... 600/436 |
| 5,662,109 | A | * | 9/1997 | Hutson .......................... 600/427 |
| 5,709,206 | A | * | 1/1998 | Teboul .......................... 600/437 |
| 5,840,029 | A | | 11/1998 | Mazess et al. |
| 6,175,655 | B1 | | 1/2001 | George, III et al. |
| 6,275,722 | B1 | * | 8/2001 | Martin et al. ................. 600/410 |
| 6,319,202 | B1 | | 11/2001 | Inadama |
| 6,423,002 | B1 | * | 7/2002 | Hossack ....................... 600/439 |
| 6,517,484 | B1 | | 2/2003 | Wilk et al. |
| 6,527,720 | B1 | | 3/2003 | Ustuner et al. |
| 6,530,686 | B1 | | 3/2003 | Nakamura |
| 6,556,695 | B1 | | 4/2003 | Packer et al. |
| 6,685,644 | B2 | * | 2/2004 | Seo et al. ...................... 600/447 |

\* cited by examiner

*Primary Examiner* — Peter Luong
(74) *Attorney, Agent, or Firm* — Leffert Jay & Polglaze, PA

(57) ABSTRACT

An imaging system uses sensors to traverse an external portion of an object to generate a three dimensional image of the object.

16 Claims, 2 Drawing Sheets

MEDICAL IMAGING DEVICE AND METHOD

FIELD

The present invention relates generally to imaging and in particular the present invention relates to medical imaging.

BACKGROUND

It has become increasingly common to use different medical imaging devices in the diagnosis of injuries and diseases. Such imaging devices include by way of example only and not by way of limitation, x-rays, ultrasound, magnetic resonance imaging. The resultant images from such imaging devices, while they can show such injuries and the like, tend to require extra interpretation by experts in order to confirm diagnoses. Further, the images obtained through the use of such imaging devices can be unclear, fuzzy, or of low resolution. They are further typically viewable or readable only using special machinery, and can have significant time and expense if they are to be duplicated.

For the reasons stated above, and for other reasons stated below which will become apparent to those skilled in the art upon reading and understanding the present specification, there is a need in the art for an improved external imaging system, and for an imaging system to provide external and internal imaging.

SUMMARY

The various embodiments described herein include an imaging system with a sensor ring and a motor for moving the ring to move the sensors around an object within the ring.

Embodiments of the invention include apparatus and methods of varying scope.

DETAILED DESCRIPTION

Figure 1:
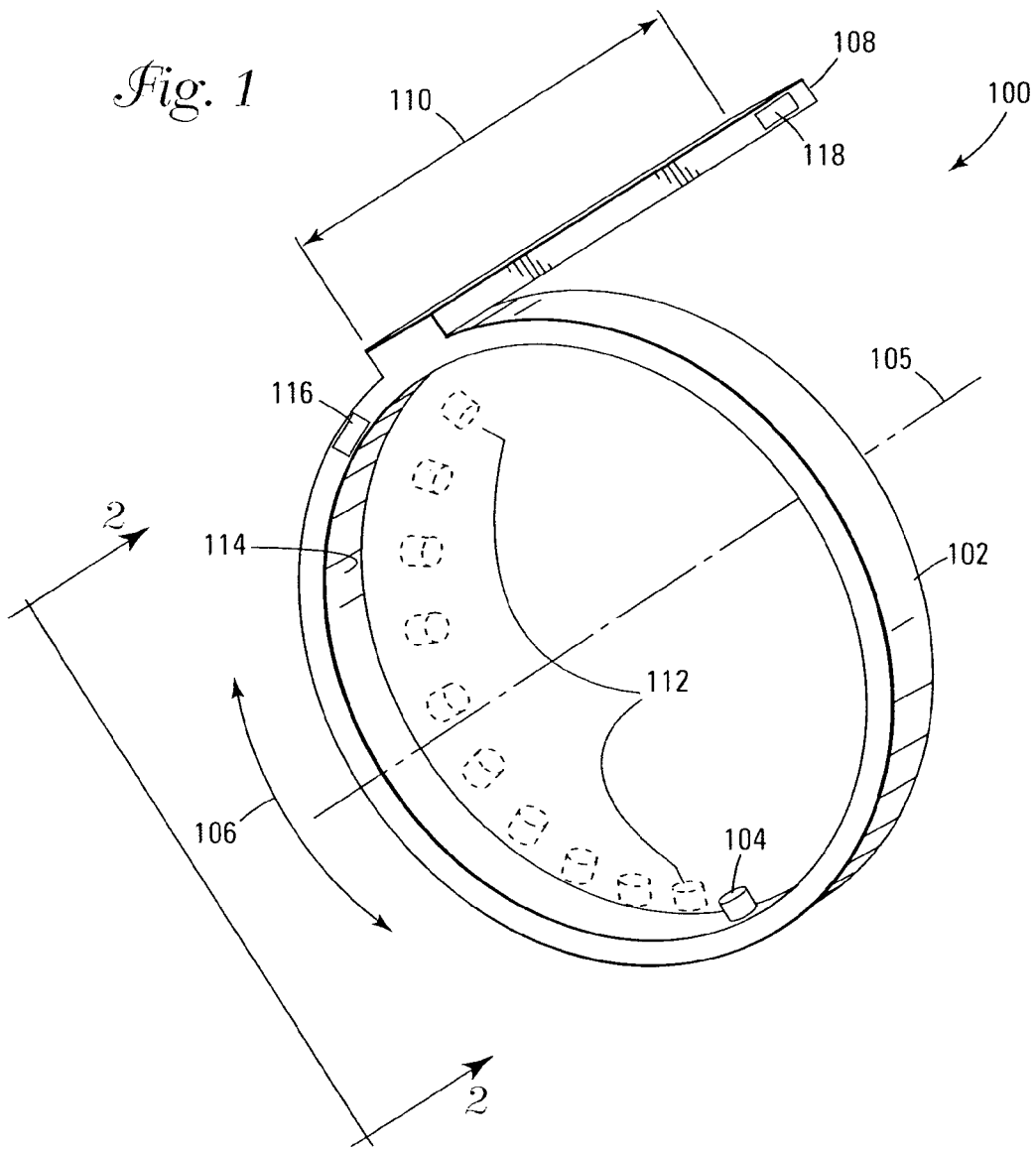
FIG. 1 is a perspective view of an imaging apparatus according to one embodiment of the present invention.

In the following detailed description of the invention, reference is made to the accompanying drawings that form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention.

Some portions of the detailed descriptions which follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. It should be borne in mind, however, that all of these and similar terms are to be associated with the appropriate physical quantities and are merely convenient labels applied to these quantities.

Unless specifically stated otherwise as apparent from the following discussions, it is appreciated that throughout the present invention, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The following detailed description is, therefore, not to be taken in a limiting sense, and the scope of the present invention is defined only by the appended claims, along with the full scope of equivalents to which such claims are entitled.

A medical imaging system obtains graphical information on an object, such as an extremity like an arm or leg, that can be combined with internal imaging of, for example, bone fractures and structures within the extremity. The various embodiments of the system operate in conjunction with internal imaging devices. An input device for the system comprises a mechanical sleeve or ring of a sufficient size to accommodate a body or part thereof for imaging. Multiple sensors send out signals and receive back data that is sent to a processor, and processed to create a three dimensional image of the extremity or body involved in the imaging. The resulting image is presented for display on a monitor or other screen for viewing, and can be manipulated using software.

FIG. 1 is a perspective view of one embodiment of an imaging system 100. Imaging system 100 comprises a sensor ring 102 having mounted thereon and facing the inner portion of the ring 102 at least one sensor 104. Ring 102 is rotatable about its longitudinal axis 105 in the direction indicated by arrow 106. Ring 102 is further movable along its longitudinal axis 105 in the direction indicated by arrow 110. To move ring 102 laterally along axis 105, ring 102 is operatively connected to linear bar 108. A motor such as motors 116, or other component suitable to create movement of the ring 102 both rotationally and translationally, is operatively connected to control motion of the ring 102. Such a motor may be an electric motor or the like. A second motor 18 operatively connected to control another aspect of motion of the ring may be used. The position of the rotational and translational movement of the ring is also stored and processed by the processor receiving signals from the motor or motors, so that the relative positioning of the ring with respect to the object being imaged is known. This allows a better representation of the object.

Figure 3:
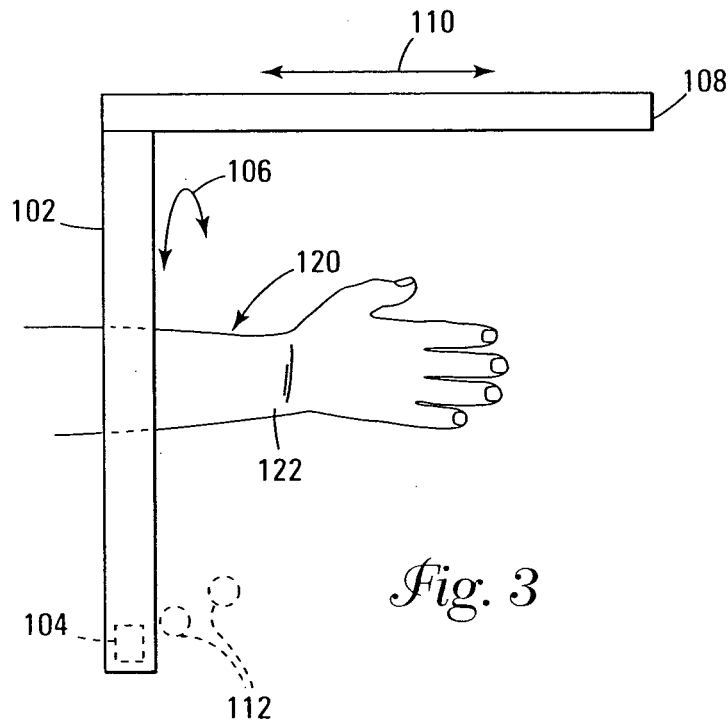
FIG. 3 is a view of the imaging apparatus of FIG. 2 taken along lines 3-3 thereof.

To render a three dimensional image, the sensors 104 are mounted in a position so that partial or complete rotation and/or translation of the ring 102 moves the sensors 104 through a complete imaging of a stationary subject. The phantom sensor positions 112 shown in FIGS. 1 and 3 illustrate sensor positioning as the ring 102 rotates and translates as has been described. In one embodiment, sensors such as sensors 104 are positioned in spaced apart relation around the inner circumference 114 of ring 102, and the sensors 104 encircle the subject of the imaging. The ring 102 undergoes translational movement along the axis 105. The sensor data and the translational position of the sensor ring are processed by a operatively connected processor such as in a computer or the like, as is described in greater detail below. The positional data is combined to form a three dimensional image of the external surface of the subject of the imaging.

In another embodiment, the ring 102 itself contains a suitable number of sensors 104 to perform a partial imaging of the complete circumference of the ring 102. The ring may also undergo in one embodiment translational motion to move the ring along a length of a subject to be imaged. The translational and rotational motion allows a stationary subject or part of a subject to be imaged without motion on the part of the subject.

The sensors 104 send out sensor waves, specific to the type of sensor, to determine the edge of an object that is placed in the imaging system. The external image of the object in the sleeve is obtained through a series of sensor readings, each of which are transmitted to and processed by a processor or other computing device.

In one embodiment, ultrasonic sensors are used. The ultrasonic sensors emit waves that strike and reflect from an external surface of an object in the sensor range, and the reflected signals are received back at the sensor. The received data are transmitted to and processed by a computer or other processor to interpret the data, and to generate a three dimensional image of the subject. Ultrasonic sensors operate by transmitting a voltage signal. The reflected voltage signals that return to the sensor vary with an object distance from the sensor. Return signals received by the sensors are processed by a microprocessor, along with data received from other sensors, and using known initial and final positions and direction and speed of motion which is also known, to create a three dimensional representation of an object within the sensor field of detection.

Figure 2:
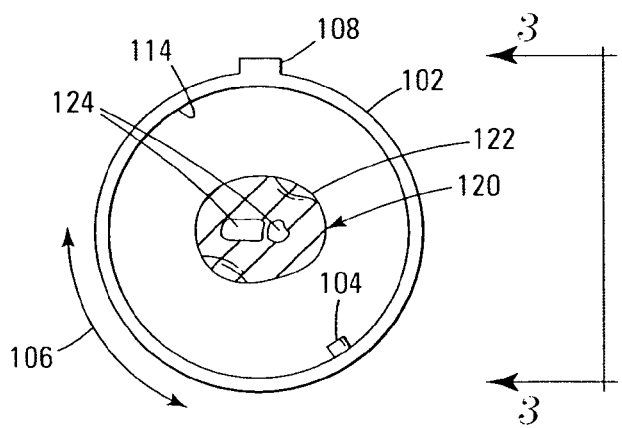
FIG. 2 is a view of the imaging apparatus embodiment of FIG. 1 taken along lines 2-2 thereof.

FIG. 2 is a view of the imaging system 100 of FIG. 1 shown along lines 2-2 thereof, with an extremity 120 shown in cross section inserted within the interior of the ring 102. In FIG. 2, extremity 120 has an external surface 122 and internal features 124. Ring 102 is rotatable in the direction of arrow 106. When ring 102 rotates, sensor 104 is moved in position relative to the extremity 120. The sensor 104 gathers sensor readings for a rotational position that is known by a processor or other computing device to which the sensor is operatively connected, as will be described in further detail below. FIG. 3 is a view of the imaging system 100 of FIG. 2 shown along lines 3-3 thereof. Linear movement of ring 102 is made along the bar 108 in the direction indicated by arrow 110. The stationary subject 120 is placed into the imaging system, or a part of the body of a subject is placed in the imaging system, and a series of movements while sensing take place that result in the imaging of a three dimensional subject.

Figure 4:
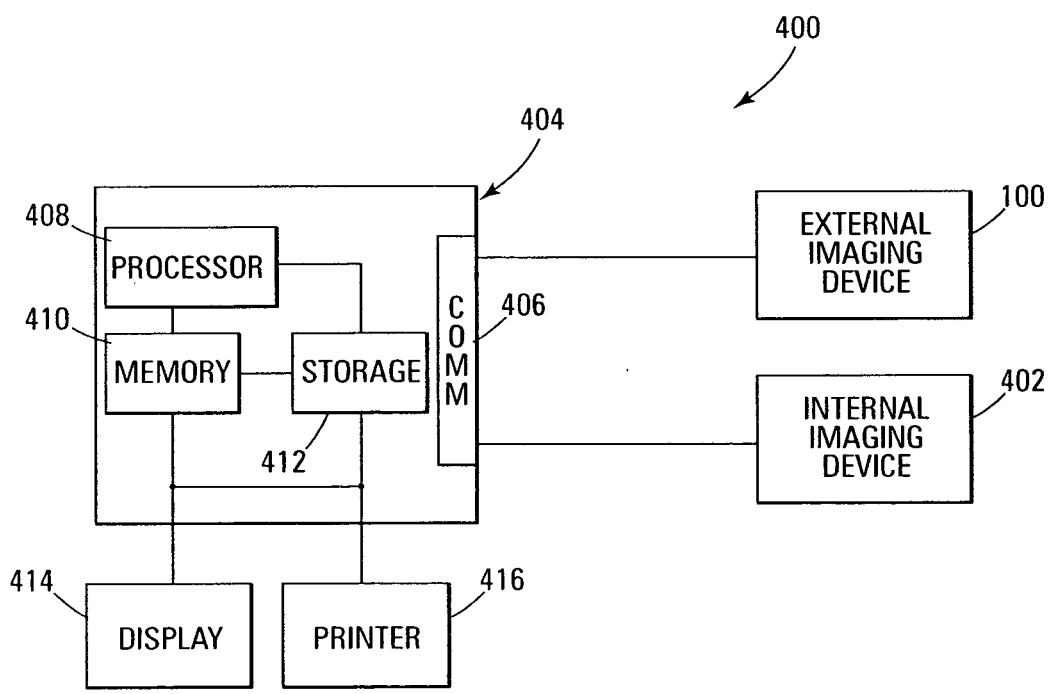
FIG. 4 is a block diagram of an imaging apparatus according to another embodiment of the present invention.

FIG. 4 is a block diagram of an imaging system 400 according to another embodiment if the present invention. An external imaging device such as device 100 shown in FIGS. 1-3 is connected along with an internal imaging device 402 to a computer 404. Computer 404 comprises a communications module or panel 406 for connection to the external 100 and internal 402 imaging devices, and a processor 408, memory 410, and storage 412. Computer 404 can be operatively connected to a display 414 and a printer 416.

The internal imaging device 402 generates an image of internal features of a subject or object such as subject 120 described above. In combination with external imaging device 100, the internal and external images provide a complete view of the subject 120 when the data from each system 100 and 402 is processed. Once the data from each of systems 100 and 402 is processed, the resulting images are combined in software, and a composite or combination image of both the external and internal features of the subject is generated. In one embodiment, position of the internal features of the subject is made by comparison with known anatomical replicas. In another embodiment, a common point of reference is used to align the external and internal images before overlaying one image with the other. The combined or composite image may then be stored in the storage 412 of computer 404, and may also be displayed on display 414 or printed on printer 416.

The resultant three dimensional images can in another embodiment, in combination with another imaging device such as a magnetic resonance image (MRI), ultrasound, X-ray, or the like, can be cross sectioned to display internal features such as a bone within the extremity to determine damage to muscles, nerves, or other tissue.

Overlaying of images from one or more of an MRI, and ultrasound, and an x-ray, in combination with the data retrieved through the use of the embodiments of the present invention, allows the presentation and generation of a complete image of the extremity or body part of the subject. This combination image is then saved in a picture format, and can be printed immediately using a printer. Multiple copies of the image are capable of being quickly and easily printed. The resulting image is more clear and easier to read and interpret than current images. Further, the resulting images make the job of explaining and showing problems or diagnoses to lay persons, such as patients or loved ones of a patient. Using the images generated by the various embodiments of the present invention, simulated surgery can be shown or performed. Specifically, since a three dimensional representation of the extremity or body part has been generated in a computer readable format, the representation can be manipulated, that is it can be rotated to be viewed or printed from any one of a multitude of angles and perspectives.

A program or set of machine readable instructions stored in storage of the computer, and executable by the processor in the memory of the computer, function to receive data from the external imaging device 100 and the internal imaging device 402, and to combine the images of an object from each of the two devices 100 and 402 to generate a three dimensional representation of an object that is sensed by each of the devices 100 and 402. In one embodiment, the external image generated by external imaging device 100 is overlaid onto the internal image generated by the internal imaging device 402, so that a combination image showing both the external and internal features of the object being imaged is created. This combination image is displayable on the display 414, and can be saved in image format such as bitmap (bmp), JPG, or the like, for later viewing, and for printing using printer 416. High resolution printers are capable of quickly printing images with very high resolutions, so that a combination image can be viewed as well as printed nearly instantaneously upon its generation.

Further, the computer program for overlaying internal and external images, since the external images and internal images are three dimensional in nature, shows and generates images that contain more information in a more easily understood format. A representation of both the internal and external features of an object, such as a limb or the like, shows not only bone structure, but skin and muscle features as well, with each of the features of the limb being shown in their relative positions with respect to one another. In the embodiments of the present invention, therefore, a more complete picture of an injury is generated. That is to say, the location of a fracture is shown precisely with respect not only to the remaining bones or other internal structures of the body, but also with respect to the external features. This allows a more precise view and explanation of fractures and the like, and serves as an aid in teaching, simulating surgery, diagnosis, and the like.

In operation, the imaging systems of the present invention work as follows. A subject is placed within a sensor ring such as ring 102. Sensors 104 on the ring emit sensor waves, which reflect off of the subject and are received back at the sensors. The sensors are connected to transmit data about received return waves to a microprocessor or other computer for interpretation. Multiple sensor readings are obtained while the ring 102 is moved in at least two motions, one motion being a rotational motion about the subject, and another motion being a translational linear motion along an axis normal to a rotation vector of the ring. The sensors and the motion of the sensors allows the imaging system to image the external surface of the subject. In combination with an internal image of the subject, which may be obtained by way of example only and not by way of limitation by magnetic resonance imaging, ultrasound, X-ray, or the like, an complete three dimensional image of the internal features and external shape of an object is generated. This three dimensional image is the capable of being stored, printed, displayed, and manipulated by software. For example, the image can be rotated, and multiple angle images of the subject can be printed so that views from multiple angles may be observed. In another embodiment, the file can be saved with all the images having the flexibility of showing or not showing a desired portion of the combined image. The processor is able to differentiate features on the internal image and save each image as a separate object, and can turn each object on or off as required or desired. For instance a surgeon may need to filter features that are at the moment irrelevant to an analysis, such as a blood vessel when inspecting muscle integrity, muscle mass when inspecting an aneurysm, and the like.

The methods described herein may be implemented in whole or in part in various embodiments in a machine readable medium comprising machine readable instructions for causing a computer such as computer 404 shown in FIG. 4 to perform the methods. The computer programs run on the central processing unit 408 out of main memory 410, and may be transferred to main memory from permanent storage 412 via disk drive or CD-ROM drive when stored on removable media or via a network connection or modem connection when stored outside of the computer 404, or via other types of computer or machine readable media from which it can be read and utilized.

Such machine readable media may include software modules and computer programs. The computer programs may comprise multiple modules or objects to perform the methods or the functions of various apparatuses of FIGS. 1, 2, 3, and 4. The type of computer programming languages used to write the code may vary between procedural code type languages to object oriented languages. The files or objects need not have a one to one correspondence to the modules or method steps described depending on the desires of the programmer. Further, the method and apparatus may comprise combinations of software, hardware and firmware as is well known to those skilled in the art.

CONCLUSION

Methods and apparatus for generating three dimensional printable representations of body parts or the like have been described that include generating both internal and external features in an easily readable and manipulable format.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

What is claimed:
1. An imaging system, comprising:
a first imaging device for imaging an external surface of an object to be imaged;
a second imaging device for imaging internal features of the object to be imaged; and
a processor operatively connected to the first imaging device and to the second imaging device, the processor to combine images from the first imaging device and the second imaging device to create a three dimensional image of the external and internal features of the object to be imaged;
wherein the first imaging device comprises:
a sensor ring having a plurality of sensors mounted thereon to send out signals and to receive back reflected signals pertaining to data of external features of the object within the ring;
a first motor operatively connected to the sensor ring to move the ring about its longitudinal axis to rotate the ring about the object within the ring; and
a second motor to move the ring translationally along the longitudinal axis.

2. The imaging system of claim 1, wherein the second imaging device is a magnetic resonance imaging device.

3. The imaging system of claim 1, wherein the second imaging device is an ultrasound device.

4. The imaging system of claim 1, wherein the second imaging device is an X-ray device.

5. The imaging system of claim 1, wherein the sensors are ultrasonic sensors.

6. The imaging system of claim 1, and further comprising:
a printer operatively connected to a computer having a processor coupled to the imaging system, the printer to print generated images.

7. A method of imaging, comprising:
obtaining a three dimensional internal image of an object;
obtaining a three dimensional external image of the object;
processing the images in a processor; and
combining the internal and external images to form a composite image;
wherein obtaining the three dimensional external image of the object comprises:
placing the object into a sensor ring, the sensor ring having a plurality of sensors mounted thereon to send out signals and to receive back reflected signals pertaining to data of external features of the object within the ring;
rotating the sensor ring about a longitudinal axis of the sensor ring to image a circumference of the object;
translating the sensor ring along the longitudinal axis to image a length of the object;

sending out signals from sensors of the sensor ring; and sensing external image information from signals reflected from the external features of the object and received back at the sensors of the sensor ring.

8. The method of claim 7, and further comprising:

displaying the composite image on a display device.

9. The method of claim 7, and further comprising:

manipulating the image to view the image from a desired angle or angles; and printing any image views desired.

10. The method of claim 7, and further comprising:

saving the composite image in a machine readable format.

11. The method of claim 7, wherein the internal image is a magnetic resonance image.

12. The method of claim 7, wherein the internal image is an ultrasound image.

13. The method of claim 7, and further comprising:

overlaying the external image with a magnetic resonance image; and saving a combined image in a machine readable format.

14. A method of generating an image of an object, comprising:

obtaining an internal image of the object;

obtaining a three dimensional external image of the object;

overlaying the internal image with the three dimensional external image to generate a combined image; and saving the combined image in a machine readable format;

wherein obtaining the three dimensional external image of the object comprises:

placing the object into a sensor ring, the sensor ring having a plurality of sensors mounted thereon to send out signals and to receive back reflected signals pertaining to data of external features of the object within the ring;

rotating the sensor ring about a longitudinal axis of the sensor ring to image a circumference of the object;

translating the sensor ring along the longitudinal axis to image a length of the object;

sending out signals from sensors of the sensor ring; and sensing external image information from signals reflected from the external features of the object and received back at the sensors of the sensor ring.

15. The method of claim 14, wherein saving comprises saving the combined image as a plurality of individual images.

16. The method of claim 15, and further comprising:

selecting one or more of the plurality of individual images for viewing.

* * * * *